United States Patent [19]

Martell

[11] Patent Number: 4,897,083
[45] Date of Patent: Jan. 30, 1990

[54] SYRINGE NEEDLE GUARD

[76] Inventor: Michael D. Martell, 6297 Sandoval Ave., Riverside, Calif. 92509

[21] Appl. No.: 191,565

[22] Filed: May 9, 1988

[51] Int. Cl.⁴ .............................................. A61M 5/32
[52] U.S. Cl. ................................... 604/192; 604/198; 604/263
[58] Field of Search ............... 604/192, 187, 198, 263, 604/197

[56] References Cited

U.S. PATENT DOCUMENTS

| | | |
|---|---|---|
| 2,571,653 | 10/1951 | Bastien . |
| 3,073,306 | 1/1963 | Linder . |
| 4,356,822 | 11/1982 | Winstead-Hall . |
| 4,416,663 | 11/1983 | Hall . |
| 4,425,120 | 1/1984 | Sampson ............................ 604/197 |
| 4,573,976 | 3/1986 | Sampson et al. .................... 604/198 |
| 4,631,057 | 12/1986 | Mitchell .............................. 604/198 |
| 4,681,567 | 7/1987 | Masters ............................... 604/198 |
| 4,735,311 | 4/1988 | Lowe et al. ..................... 604/198 X |
| 4,804,372 | 2/1989 | Laico et al. ......................... 604/198 |

Primary Examiner—John D. Yasko
Attorney, Agent, or Firm—Poms, Smith, Lande & Rose

[57] ABSTRACT

A telescoping guard for a hypodermic syringe needle assembly has an inner section that is securely connected to the upper section of a standard needle assembly hub. The guard can be telescopically extended to afford full protection for the cannula of the needle assembly, and can be contracted to clear the cannula for use without any interference with the syringe barrel. The guard allows use of a standard cannula cap on the standard needle assembly.

15 Claims, 2 Drawing Sheets

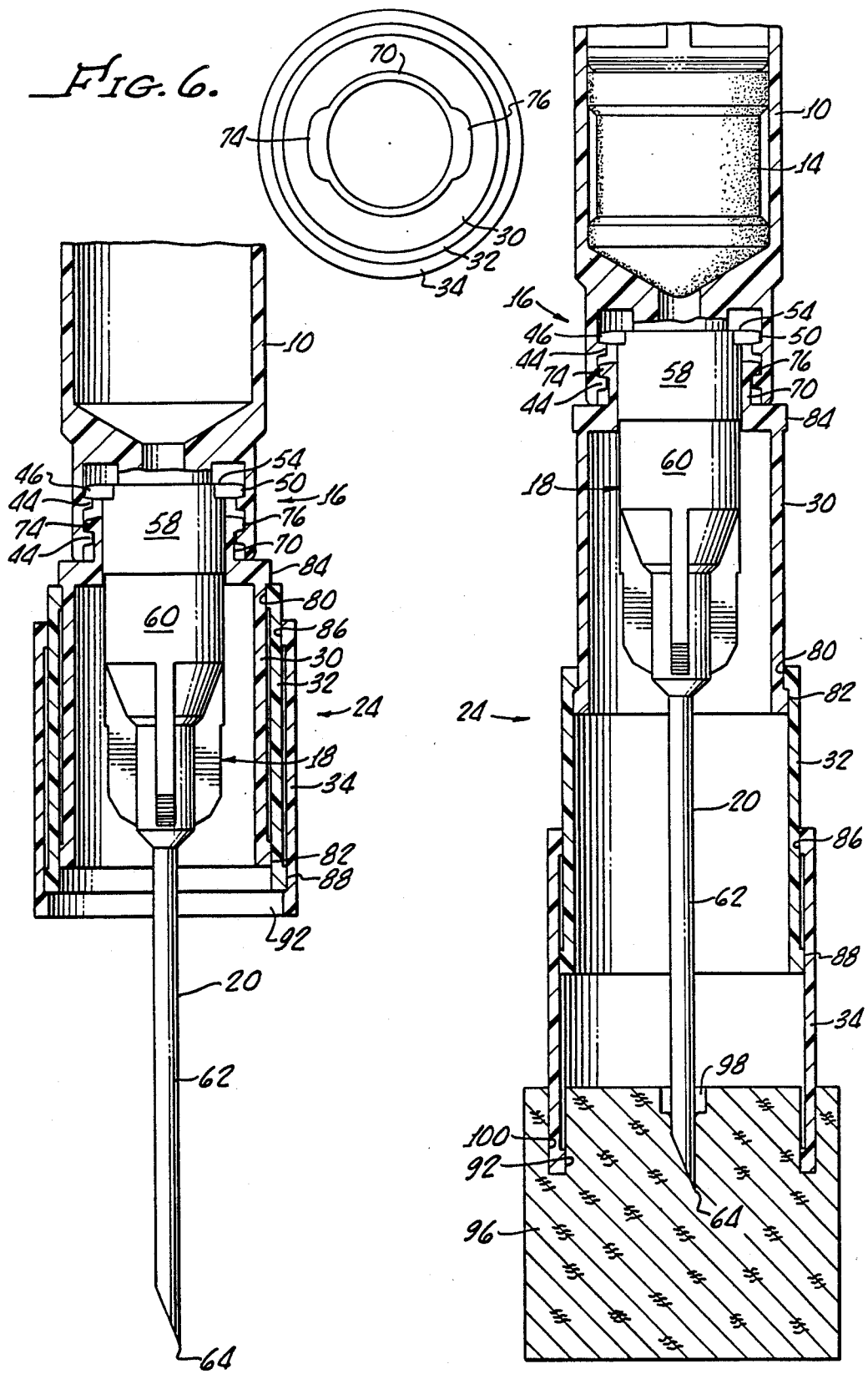

SYRINGE NEEDLE GUARD

BACKGROUND OF THE INVENTION

The present invention relates to hypodermic syringe needle assemblies, and more particularly concerns a needle assembly that has an improved protective sleeve to guard against inadvertent contact with the end of the cannula.

The standard hypodermic syringe includes a barrel and plunger and a needle assembly having a hub that is readily attachable to and detachable from an end of the barrel. The needle hub mounts the cannula, and in the standard needle assembly, a cannula guard cap is provided that is a hand tight friction fit on the hub. The cannula cap is removed for use of the syringe, and after use the cap may be replaced, or the needle may be inserted into a cork to seal the contents of the syringe. The required handling of the needle assembly after use, whether by replacing the cannula cap or inserting the cannula into a cork, exposes the health care worker to the possibility of accidental needle sticks. With the highly publicized spreading of blood-borne diseases, dangers of such accidental needle sticks are becoming of greater concern. The modern health care worker faces increased risk of contracting life threatening disease through on-the-job exposure at least partly due to accidental needle sticks.

The increased danger has stimulated increased effort toward providing needle assembly protection. Different types of protective devices have been suggested. Many of such devices, however, require some type of structure that is connected to or mounted upon the barrel of the syringe itself and remain connected to the barrel during use and handling of the syringe. This causes significant interference with the handling and use of the syringe, since the standard, relatively smooth and relatively small diameter barrel has now become encumbered with a protective device, which may prevent direct contact of the operator's fingers with the barrel itself. Other arrangements for needle protection, recognizing the problem that stems from the location of protection mounting structure on the syringe barrel, have provided special needle and guard assemblies requiring specially manufactured needles which are considerably longer and more costly than the standard needle assembly.

A widely used standard needle assembly includes a needle hub having an upper end that is formed with an arrangement for connecting the hub to an end of the syringe barrel, and having a lower end to which is fixedly secured the cannula. A standard syringe barrel has an end formed with what is commonly known as a leur tip. The leur tip is available in two forms. A leur slip tip is an elongated, slightly tapered connecting fitting or neck extending from the end of the barrel and formed integrally therewith. The slip tip taper is a hand tight friction fit with the interior of the upper section of the needle assembly hub, which thus can be firmly connected to or removed from the syringe barrel. In a second form of leur tip, the tapered connecting fitting or neck remains the same, but is surrounded by an internally threaded sleeve radially spaced from the slip tip neck. The standard needle assembly hub includes an upper flange having a pair of diametrically opposed, radially outwardly extending ears, which effectively form a pair of thread elements that threadedly engage the internal threads on the leur tip threaded sleeve. In this arrangement the needle assembly hub can be threadedly engaged with the leur tip, and, at the same time, connected to the tip neck with a tight frictional fit for more firm securement. The widely used standard needle assembly thus is particularly configured for use with the widely used leur tip syringe of either configuration. Therefore, it is important that a needle guard be usable with the standard needle assembly and the standard leur tip syringe.

Accordingly, it is an object of the present invention to provide a needle guard that may be used with standard needle assemblies and syringes and avoids problems of prior devices.

SUMMARY OF THE INVENTION

In carrying out principles of the present invention, in accordance with a preferred embodiment thereof, a protective sleeve is made for use with a needle assembly, which assembly has a hub for connection to a syringe barrel and a cannula on a lower section. The sleeve has an inner end secured to and circumscribing an upper section of the hub, and has an outer end extending to the tip of the cannula when the sleeve is longitudinally extended. The sleeve is longitudinally collapsible to a contracted position in which the sleeve outer end is positioned inwardly of the cannula tip to expose the cannula tip for use. The sleeve is mounted to the needle assembly of the standard needle, and does not rely on any connection to the syringe barrel.

BRIEF DESCRIPTION OF THE DRAWINGS

FIG. 4 shows the parts of FIG. 3 with the cannula cap removed and the sleeve contracted;

FIG. 5 illustrates the application of a cannula protecting cork to a cannula having the protective sleeve secured thereto; and FIG. 6 is a top plan view of the protective sleeve.

DETAILED DESCRIPTION OF THE INVENTION

Figure 1:
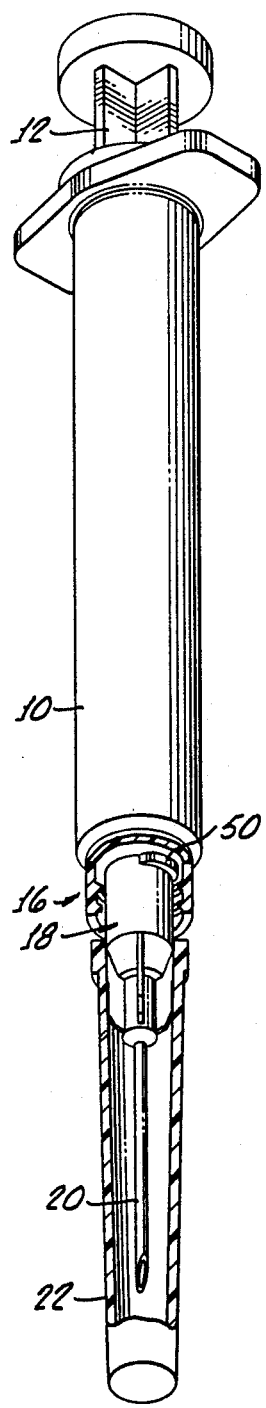
FIG. 1 shows a standard syringe and needle assembly with a cannula cap.

A common form of hypodermic syringe together with a standard needle assembly is illustrated in FIG. 1. The syringe is formed with a tubular barrel 10 in which is slidably mounted a handle 12 having a plunger 14 (see FIGS. 3 and 5) at a lower end thereof forming a slidable but sealing fit within the interior of the barrel. The end of the barrel includes a leur tip generally indicated at 16 to which is connected a standard needle assembly including a needle hub 18 having a cannula 20 secured thereto. A cannula cap 22 protects the cannula tip and is a hand tight friction fit on a lower portion of the hub 18.

Figure 2:
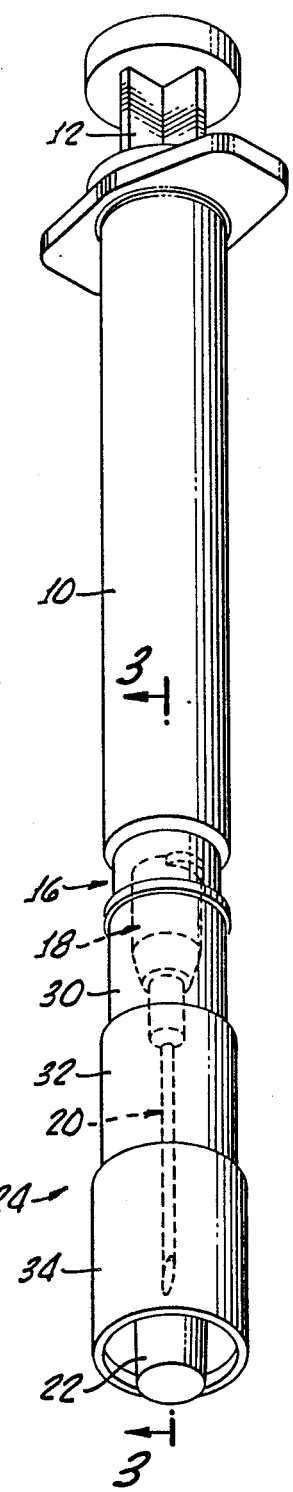
FIG. 2 illustrates the assembly of FIG. 1 with the protective sleeve of the present invention secured thereto in extended position.

FIG. 2 illustrates the assembly of FIG. 1 having the telescoping needle guard of the present invention secured thereto. The needle guard 24 is formed of three telescoping sections comprising an inner section 30, an intermediate section 32, and an outer end section 34. The inner section is secured to an upper portion of the needle assembly hub 18 above the upper end of the cannula cap 22.

Figure 3:
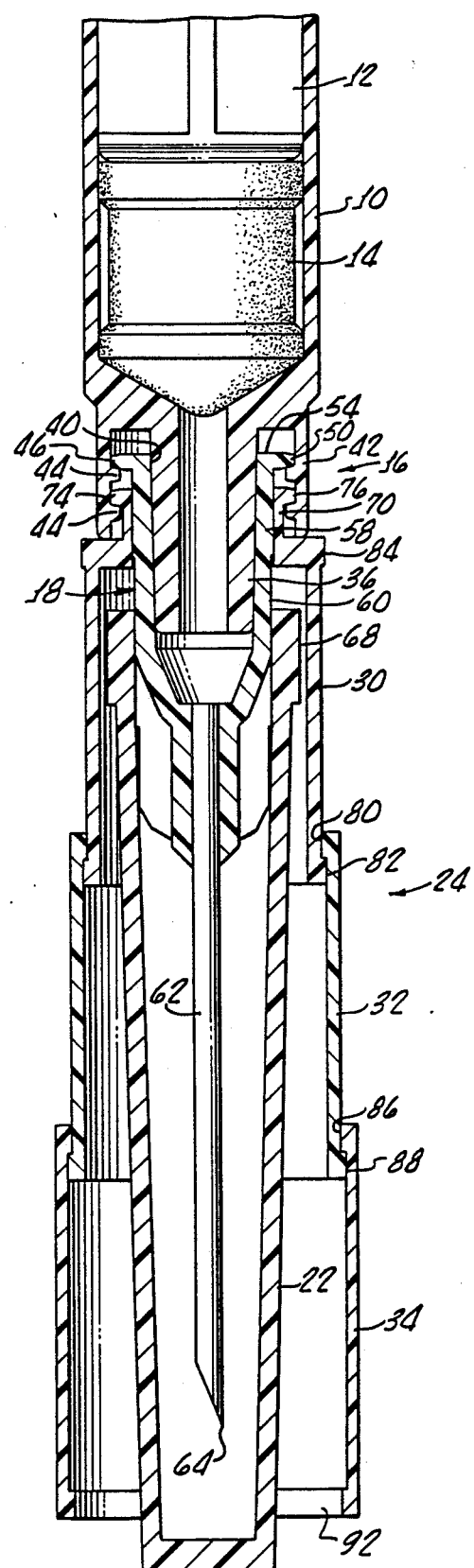
FIG. 3 is an enlarged sectional view of part of the syringe, needle, assembly and protective sleeve, with the sleeve extended.

As shown in the enlarged detailed drawing of FIG. 3, the standard leur tip includes a leur tip neck 36 formed integrally with the bottom of barrel 10 and providing a tapered connection fitting for communicating with and secure attachment to the interior of the needle assembly hub 18. The hub has a bore with a tapered surface 40 that mates with the outer surface of the leur tip neck 36 and may be a hand tight fit on the neck to securely hold the needle assembly on the leur tip neck. In one form of leur tip (not shown), the tip has only the neck 36. The tight frictional fit between the neck and hub bore is sufficient, of itself, to secure the needle assembly to the syringe barrel. In the form of leur tip shown in the drawings the neck 36 is surrounded by a short cylindrical sleeve 42 that extends from the barrel a distance less than the distance for which the neck extends. The sleeve 42 has a relatively high pitch internal thread 44 formed to cooperate with a pair of oppositely disposed radially outwardly projecting ears 46,50 formed on an upper flange 54 of the upper portion of the needle assembly hub. Thus by inserting the leur tip neck 36 into the bore 40 and turning the hub 18, the teeth or ears 46,50 become threadedly engaged with the internal threads 44, and further draw the needle hub further up onto the leur tip neck to more tightly hold the needle assembly in its secured position with the syringe barrel.

The standard needle assembly hub includes a relatively larger exterior diameter upper section 58 and a slightly smaller exterior diameter lower section 60 that circumscribes the lower portion of the hub bore 40. To the lowermost end of the hub 18 is secured the cannula 20, having an insertion tip 64. Commonly a cannula cap 22 is provided in the form of a tapered tube closed at an end adjacent the insertion tip and open at its upper end. The upper end of the cannula cap has an enlarged flange 68 circumscribing a cap opening that is a hand tight friction fit on the smaller diameter lower section 60 of the needle assembly hub.

The telescoping guard sleeve or protective sleeve 24 of the present invention includes the inner section 30, having a necked down connecting section 70 at its uppermost end. The necked down connecting section 70 defines an interior bore of a diameter smaller than the interior diameter of the remainder of section 30. The bore of connecting section 70 is a hand tight friction fit on the larger diameter upper section 58 of the hub. Connecting section 70 is formed at its uppermost end with a pair of diametrically opposed radially outwardly projecting ears 74,76 (FIG. 6), which threadedly engage the internal threads 44 of the threaded leur tip sleeve 42. The ears 74,76 of the guard sleeve connecting section are spaced from the ears 46,50 of the hub assembly when the guard sleeve is assembled on the hub so that both pairs of ears may engage the inner threads of the leur tip threaded sleeve.

The lower portion of the inner section 30 of the guard sleeve has an interior diameter that is larger than the outer diameter of the lower section 60 of the hub, and thus provides an annular space for reception of the enlarged inner end 58 of the cannula cap.

Intermediate sleeve 32 of the guard sleeve has an inwardly projecting small annular flange 80 that circumscribes its periphery and is a snug, sliding fit on the exterior surface of the lower portion of inner sleeve section 30. Inner sleeve section 30 is formed with a small radially outwardly extending annular flange 82 at its lower end that cooperates with flange 80 to retain the intermediate section in its slidable relation with respect to the inner section 30. The latter is also formed with a small annular radially outwardly extending protrusion 84, adjacent connecting section 70, that helps to retain the intermediate section on the inner section.

The outer end section 34 of the guard sleeve is formed with a radially inwardly extending small annular flange 86 that is a snug sliding fit on the exterior surface of intermediate section 32 and cooperates with a radially outwardly extending small annular flange 88 on the outer end of intermediate section 32 to keep the intermediate and outer guard sleeve sections in engagement. Outer end section 34 is also formed with a radially inwardly projecting small annular flange 92 that helps retain the outer end section 34 on the intermediate section 32 when the several sections collapse from the extended position of FIG. 3 to the contracted position of FIG. 4. The sections of the guard sleeve are made of a suitable plastic, such as polycarbonate. The sections have sufficient resilience to allow the interengaging sections of the guard sleeve to be assembled one upon the other by forcibly distorting the interengaging flanges 80,82, 86,88.

The described needle guard sleeve, with its three sections telescopically interconnected, is assembled to the needle hub with the cannula cap removed from the hub. Connecting section 70 of the inner end of the innermost sleeve section is forced upon and along the upper, larger diameter hub section 58 and is a strong hand tight fit thereon. By this means the telescoping guard will remain attached to the hub during all subsequent operation with the needle assembly. After attachment of the telescoping sleeve to the hub, the cannula cap may be inserted into the sleeve to frictionally engage and be secured to the smaller diameter lower section 60 of the hub, with the upper open end of the cannula cap being received within the annular space between the hub lower section and the relatively larger diameter of the sleeve inner section. Now the combination of needle hub, cannula, telescopic guard sleeve and cannula cap, may be readily assembled to the leur tip, whether the tip has solely the leur tip neck or includes both the leur tip neck and the leur tip threaded sleeve. The assembly is secured to the leur tip just as if the telescoping guard sleeve was not attached to the needle assembly hub. Where the leur tip has no threaded sleeve, the sole connection between the guarded needle assembly and the syringe is by means of the friction fit of the tapered leur tip neck within the tapered bore of the needle assembly hub. Where the syringe has a leur tip which includes a threaded sleeve, both the needle assembly hub and the inner section of the telescopic guard sleeve may threadedly engage the leur tip threads to more firmly secure the protected needle assembly to the syringe.

With the needle hub, cannula cap, and telescopic guard sleeve attached to the syringe, the syringe may be used by merely pulling the cannula cap off the hub and, with fingers on the exterior of the telescopic guard sleeve, collapsing the latter to the position of FIG. 4. Note that in this position the sleeve sections are all substantially registered with one another so that the lowermost or outermost end of the sleeve outer end section 34 are withdrawn well back of the insertion tip of the cannula 62. The ends of all sleeve sections all are relatively close to a common plane that is perpendicular to the cannula and close to the hub. In this collapsed position of the guard sleeve, all but a small upper or innermost portion of the cannula itself is completely exposed. Further, the guard sleeve, being attached solely to the needle hub, is itself entirely below the bottom of the syringe barrel, and thus can in no way interfere with the use of the syringe by the operator, who normally holds the syringe by the barrel itself.

With the guard sleeve contracted, and the cannula cap removed, the insertion tip of the cannula is inserted into a vein or artery to withdraw blood through the needle hub and through the leur tip neck into the bottom of the barrel by retracting the plunger 14 of the syringe in standard fashion. After completion of this procedure, the cannula is withdrawn from the vein or artery, and the syringe and its needle assembly may be handled in one of several different ways to seal the syringe interior and protect against accidental needle sticks by the cannula. In one type of operation the cannula cap is returned to its place on the lower section of the hub, to thus protect the cannula. During this operation, the operator previously was subject to accident needle prick, if the narrow opening of the cannula guard should miss the cannula tip. However, with the guard sleeve of the present invention secured to the needle assembly hub, as described, immediately upon withdrawal of the needle from the vein or artery the previously contracted guard sleeve sections are extended so that the outermost sleeve end section extends to or slightly beyond the end of the insertion tip of the cannula. With the needle guard extended there is considerably less likelihood of an accidental needle stick when the cannula cap is returned to the hub. Further, with the needle guard extended, the insertion tip is well protected, even in the absence of the cannula cap. It may not be necessary to return the cannula cap to the hub, thus further ensuring against accidental needle stick which may occur during return of the cannula cap.

As mentioned above, with the guard sleeve extended, the insertion tip of the cannula is protected, with or without a cannula cap. Moreover, with the guard sleeve extended, the insertion tip of the cannula (without the cannula cap) may still be inserted into a conventional needle sealing cork, as illustrated in FIG. 5. Such a conventional needle sealing cork includes a solid body of a resilient, generally plastic material 96, having a central relatively shallow depression 98 into which the insertion tip of the cannula may be inserted to seal the interior of the syringe barrel. The standard cork is generally formed with a second radially outwardly positioned annular depression 100, which is somewhat deeper than the shallow central depression 98, so that the cork may be fixed to the standard leur tip threaded sleeve to protect the syringe tip before the needle assembly is attached to the syringe. For use with the present invention, a cork 96 is provided, but with the outer annular recess 100 made of a slightly larger diameter to receive the outer end portions of the outer end section 34 of the telescopically extended guard sleeve. Thus, after withdrawing the cannula from the vein or artery and telescopically extending the guard sleeve, the cork may be applied to the assembly by inserting the cannula insertion tip into a central portion of the shallow recess 98, causing the insertion tip to puncture the cork and to be inserted into the body of the cork. At the same time the outer end section 34 of the guard sleeve is inserted into the annular recess 100 of the cork, and thus the syringe and needle assembly are properly sealed with the cannula fully protected.

It will be seen that there has been described a significantly improved syringe needle guard sleeve. The guard sleeve is useful with the standard needle assembly, is attached solely to the hub of the standard needle assembly, and has no portion thereof extending along or around the syringe barrel. When retracted for use, the guard sleeve in no way impedes normal use of the syringe. When extended, the guard sleeve protects against needle sticks and still enables the use of the standard cannula cap or a cork for sealing the needle end and connecting to the extended needle guard sleeve. No special needle or needle construction is required, nor does this guard sleeve in any way restrict or obstruct handling of the syringe barrel.

The foregoing detailed description is to be clearly understood as given by way of illustration and example only, the spirit and scope of this invention being limited solely by the appended claims.

What is claimed is:

1. A protected needle assembly for a hypodermic syringe comprising:
    a standard needle assembly hub having upper and lower sections,
    means on said hub for connecting the assembly to a syringe barrel,
    a cannula fixed to said lower section and having an insertion tip positioned outwardly of said lower section, and
    a longitudinally extensible and collapsible protective sleeve having an inner end fixedly secured to and circumscribing said hub upper section and having an outer end radially outwardly spaced from said hub lower section and extending to said cannula insertion tip when said sleeve is longitudinally extended, said sleeve being longitudinally collapsible to a contracted position in which said sleeve outer end is positioned inwardly of said cannula tip to expose the cannula tip for use of the syringe.

2. The assembly of claim 1 wherein said hub upper section has a relatively larger exterior diameter and said hub lower section has a relatively smaller exterior diameter, and including a tubular cap extending over said cannula and having an open inner end that is a hand tight friction fit on said relatively smaller diameter lower hub section, said cap having an inner end positioned between said sleeve and said lower hub section.

3. The assembly of claim 1 wherein said sleeve inner end comprises a sleeve inner end section, said inner end section having a connecting portion frictionally secured to said hub upper section.

4. The assembly of claim 3 wherein said connecting portion has a first interior diameter, wherein said sleeve inner end section has an outer end portion having an interior diameter greater than said first interior diameter, said outer end portion extending along and being radially spaced from said hub lower section to provide an annular space between the sleeve inner end section and the hub lower section for reception of a tubular cannula cap.

5. The assembly of claim 3 wherein said connecting portion includes a bore having a reduced internal diameter, said reduced internal diameter bore being a hand tight friction fit on the exterior surface of said needle hub upper section.

6. The assembly of claim 4 including a cannula cap frictionally secured to said hub lower section between said outer end portion and said hub lower section.

7. The assembly of claim 1 wherein said connecting portion of said sleeve inner end section includes thread means extending radially outwardly.

8. The assembly of claim 7 wherein said sleeve includes three telescopically inter-engaged sections which include said sleeve inner end section, a sleeve outer end section, and an intermediate section connected to both said inner and outer end sections, said sleeve outer end forming part of said outer end section.

9. A hypodermic syringe comprising:
a syringe barrel,
a needle connecting fitting having an externally tapered neck secured to an end of said barrel, and
a guarded needle assembly secured to said fitting, said guarded needle assembly comprising:
 a hub and a cannula secured to the hub, said hub having a bore that is a tight friction fit on said connecting fitting neck, and
a longitudinally extensible and contractible guard sleeve secured to said hub, said guard sleeve being movable between a contracted position in which a major portion of the cannula is free of and extends beyond the guard sleeve, and an extended position in which the guard sleeve extends to the end of the cannula, said barrel including an internally threaded tip sleeve radially spaced from and circumscribing said needle connecting fitting, said guard sleeve including an inner section connected to said needle hub, said inner section having outwardly projecting teeth in threaded engagement with said internally threaded tip sleeve.

10. The syringe of claim 9 wherein said guard sleeve includes a plurality of telescoping sections interengaged with one another, said sections including an inner section having an end of decreased interior diameter snugly engaging the outer surface of said hub, to thereby connect the guard sleeve to the needle hub.

11. The syringe of claim 9 wherein said needle hub includes radially outwardly projecting thread means in threaded engagement with said internally threaded tip sleeve, said thread means on said hub being axially spaced from the teeth of said guard sleeve inner section.

12. The assembly of claim 10 wherein said needle hub has an upper section of a first external diameter and a lower section of a second external diameter smaller than said first external diameter, said guard sleeve inner section including a body portion having an inner diameter larger than said second external diameter of said lower hub section, thereby defining an annular space between said lower hub section and said guard sleeve body portion, and a cannula cap having an open end inserted in said annular space and frictionally secured to said lower hub section.

13. The syringe of claim 9 including a separate attachable protective cork comprising a cork body having an upper end, a substantially central recess formed in said upper end, the end of said cannula being received in said recess and penetrating the bottom thereof, said guard sleeve having an outer section, said cork upper end being detachably received in said outer section.

14. A protected needle assembly for a hypodermic syringe comprising:
a standard needle assembly having a needle hub of standard configuration, said hub having an upper section of a first external diameter and a lower section of a second external diameter smaller than said first diameter, said hub having a tapered internal bore,
a cannula secured to the hub in communication with the bore,
a radially outwardly projecting circumferential flange on said upper section, said flange having first and second oppositely disposed projections adapted to threadedly engage the threaded sleeve of a syringe leur tip, and
a multi-section telescopic guard sleeve comprising:
 an inner guard sleeve section having an inner diameter greater than the external diameter of said lower hub section, said inner guard sleeve section having an upper connecting portion with an internal diameter substantially equal to the external diameter of said hub upper section, said connecting portion being a tight friction fit upon said upper hub section, and said inner guard section being radially spaced from said lower hub section to form an annular space there between,
a second guard sleeve section slidably and telescopically connected to said inner section,
a third guard sleeve section slidably and telescopically connected to said second guard sleeve section, said guard sleeve sections being telescopically movable between a contracted position in which all of said guard sleeve sections are positioned adjacent said hub and inwardly of a major portion of said cannula, and an extended position in which the outermost one of said guard sleeve sections extends to a protective position around the end of said cannula, and
a cannula guard having an enlarged open end connected to the lower section of said hub and positioned between said lower section and said inner guard sleeve section.

15. The assembly of claim 14 wherein said upper connecting portion of said inner guard sleeve has a pair of diametrically opposed radially outwardly projecting ears for threaded engagement with the internal threads of a leur tip sleeve of a syringe.

* * * * *